United States Patent
Maschke

(10) Patent No.: US 8,265,733 B2
(45) Date of Patent: Sep. 11, 2012

(54) INJECTOR AND METHOD FOR FACILITATING IMAGING OF A PATIENT

(75) Inventor: Michael Maschke, Lonnerstadt (DE)

(73) Assignee: Siemens Aktiengesellschaft, München (DE)

(*) Notice: Subject to any disclaimer, the term of this patent is extended or adjusted under 35 U.S.C. 154(b) by 959 days.

(21) Appl. No.: 11/526,182

(22) Filed: Sep. 22, 2006

(65) Prior Publication Data

US 2007/0073139 A1    Mar. 29, 2007

(30) Foreign Application Priority Data

Sep. 23, 2005 (DE) .......................... 10 2005 045 600

(51) Int. Cl.
*A61B 6/00* (2006.01)

(52) U.S. Cl. .......... 600/431; 600/432; 600/420; 604/31; 604/67; 604/246

(58) Field of Classification Search .................. 600/407, 600/410, 431–432, 420; 604/31, 67, 246
See application file for complete search history.

(56) References Cited

U.S. PATENT DOCUMENTS

| | | | |
|---|---|---|---|
| 5,207,642 A * | 5/1993 | Orkin et al. .................... 604/65 |
| 5,391,877 A | 2/1995 | Marks | |
| 5,592,940 A | 1/1997 | Kampfe et al. | |
| 6,263,043 B1 | 7/2001 | Maschke | |
| 6,397,098 B1 * | 5/2002 | Uber et al. .................... 600/431 |
| 6,772,001 B2 | 8/2004 | Maschke | |
| 6,889,074 B2 * | 5/2005 | Uber et al. .................... 600/431 |
| 6,970,735 B2 * | 11/2005 | Uber et al. .................... 600/431 |
| 2003/0128801 A1 * | 7/2003 | Eisenberg et al. .............. 378/19 |

FOREIGN PATENT DOCUMENTS

| | | |
|---|---|---|
| DE | 695 30 035 T2 | 3/1996 |
| DE | 198 27 460 A1 | 12/1998 |

\* cited by examiner

*Primary Examiner* — Brian Casler
*Assistant Examiner* — Joel Lamprecht

(57) ABSTRACT

To facilitate imaging of a patient two different image recording methods are to be carried out at the same time. An auxiliary fluid, for example a contrast medium or a tracer, may be introduced into the body in each image recording method. The invention proposes mixing the two auxiliary fluids in situ immediately before dispensing to the patient. For this purpose it provides an injector with which the auxiliary fluids may be mixed and supplied to the patient. Devices for controlling dispensing of fluid from containers connected to the injector to produce a mixed solution may be electronically controlled by a control unit which calculates the total quantities, and optionally sub-quantities, of auxiliary fluids, which are used for a mixed solution, before activating the devices.

19 Claims, 1 Drawing Sheet

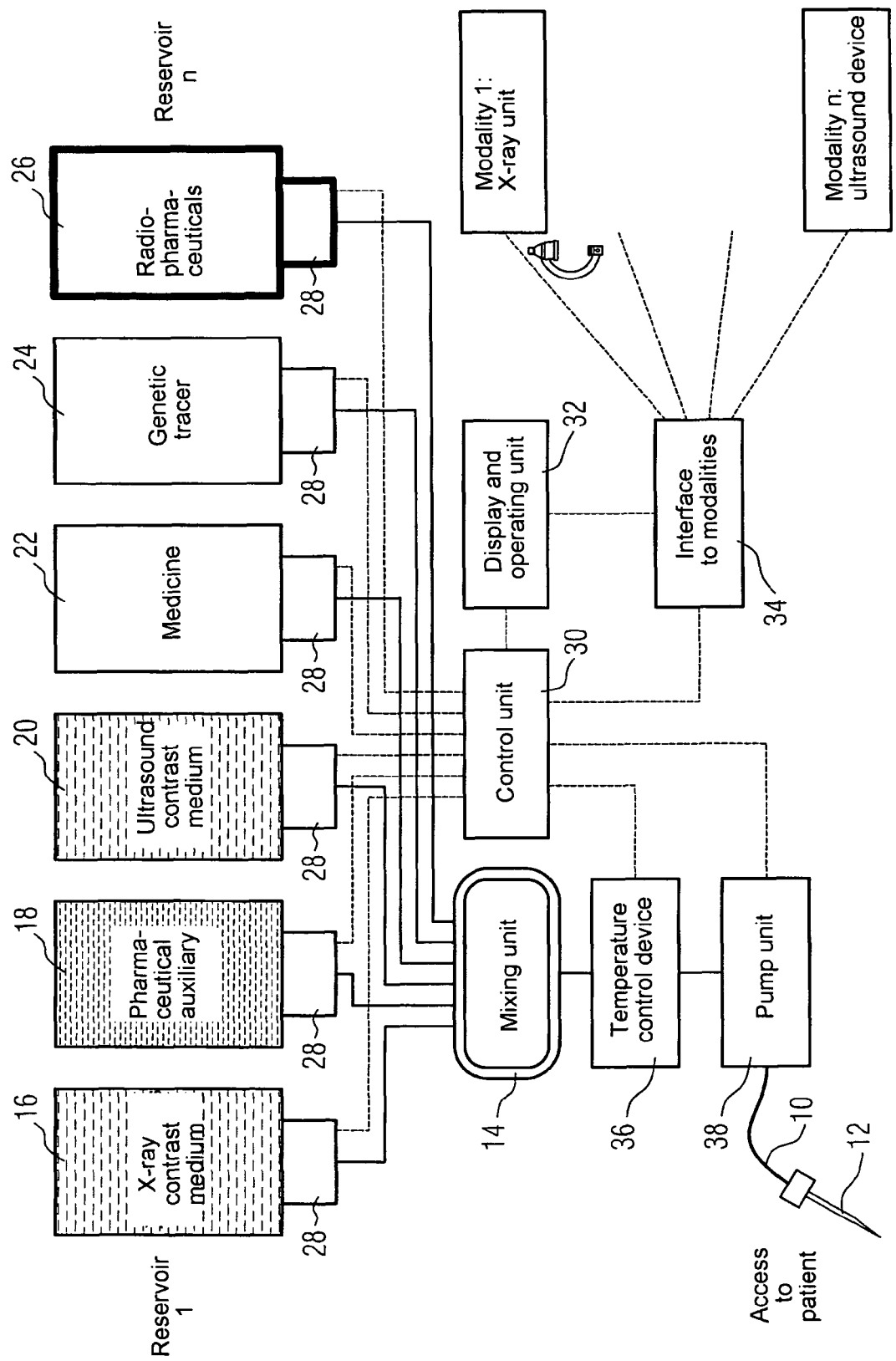

INJECTOR AND METHOD FOR FACILITATING IMAGING OF A PATIENT

CROSS REFERENCE TO RELATED APPLICATIONS

This application claims priority of German application No. 10 2005 045 600.6 DE filed Sep. 23, 2005, which is incorporated by reference herein in its entirety.

FIELD OF INVENTION

The invention relates to an injector for injecting auxiliary fluids for image recording methods into the body of a patient. It also relates to a method for facilitating imaging of a patient.

BACKGROUND OF THE INVENTION

Different imaging methods are increasingly being combined with each other in medical examinations. For example a combination of X-ray system and intravascular ultrasound (IVUS, individually described for example in DE 198 27 460 A1) is known from U.S. Pat. No. 6,772,001. The combination of nuclear magnetic resonance imaging (MRI) and X-ray installation is known from U.S. Pat. No. 6,263,043. A combination of computer tomography and positron emission tomography (PET) is known for example from U.S. Pat. No. 5,391,877. First prototypes of a combination of computer tomography with angiographic X-ray unit have been installed by Siemens.

An auxiliary fluid is used in many of these image recording methods. In the X-ray sector or in nuclear magnetic resonance imaging (extracorporeal MRI and intravascular MRI, IVMRI) contrast medium is administered into the patient's blood. In nuclear medicine (in the case of PET), so-called tracers are used.

If an envisaged combination of image recording methods should require two different auxiliary fluids to be administered, these have previously been administered separately from each other. Infusions for example are applied to the right and left arms respectively of a patient using infusion bottles.

SUMMARY OF INVENTION

The object of the invention is to facilitate implementation of the image recording methods.

For this purpose the invention provides an injector and a method according to the claims.

Like previously filed, but subsequently published, German patent application 10 2005 028882.0, the invention is based on the knowledge that the various auxiliary fluids for respective image recording methods may be administered jointly to the patient in a mixture because they mix with one another in the patient's blood anyway. A novel aspect compared with this prior application is that in this invention the mixed solution is produced in situ and, more precisely, using the injector according to the invention, with which it is also injected into the patient.

The injector according to the invention for injecting auxiliary fluids for image recording methods into the body of a patient comprises a mixing unit in which, before injection, at least two auxiliary media (fluids, fine powder) for different image recording methods may be mixed to form a mixed solution, wherein the mixed solution is conveyed in the injector to an access opening of the body, in particular to a syringe, from which the solution issues from the injector.

The mixing unit is preferably configured in such a way that at least two containers with auxiliary fluids for image recording methods may be connected to it such that they dispense fluid into the mixing unit. The term "connected" should be broadly interpreted in this case because the containers come in different shapes. What is essential is that fluid may be dispensed into the mixing unit in any case. As a rule containers of this type are standard or standardized containers which have a certain predetermined shape, so they may be held on the injector at the same time by way of a suitable predetermined holding device. In particular the auxiliary fluids are auxiliary fluids for at least two of the image recording methods from the following list:

angiographic X-ray, computer tomography, PET (Positron Emission Tomography) or SPECT (Single Positron Emission Computer Tomography), extracorporeal exposure to ultrasonic waves, intravascular ultrasound, extracorporeal MRI (Magnetic Resonance Imaging, nuclear spin) or intravascular MRI, fluorescence imaging or optical coherence tomography (OCT).

The containers may be standard containers for contrast medium, markers and tracers. A container for a medicine may also be provided, a medicine being selected for example which suppresses adverse physical reactions, such as allergic reactions, shock and cramp attacks, in response to an auxiliary fluid, or reduces the heart rate in examinations of the heart.

The standard containers can, for example, be screwed to a thread on the mixing unit. The standard containers are, for example, also bottles comprising a pierceable rubber stopper. A holding device for the bottles is then provided on the mixing unit along with hollow needles for piercing the stoppers. The fluid then passes into the mixing unit through the hollow needles.

For each container there is preferably provided a device for controlling dispensing of fluid from the connected containers into the mixing unit. These devices may be valves. It is preferably provided that the devices do not have to operated manually but instead may be electronically controlled, and in particular independently of each other. The exact mixture of the fluid may be calculated in the control unit and dispensing of the fluid controlled accordingly.

In order to be able to do this particularly effectively the control unit is preferably connected to image recording devices, from which it obtains parameter data relating to the image recording parameters, the control unit determining from the data activation signals for devices for controlling dispensing of fluid. One example of such image recording parameters is the strength of the X-ray dose used which can determine the strength of a required contrast medium. The container containing the contrast medium is accordingly activated such that the required quantity passes into the mixing unit and from the mixing unit into the syringes and hence to the patient.

The control unit may also be provided with operating state data for the image recording device, and activation signals can then be emitted as a function of the operating state data. This embodiment takes account of the fact that the two independent imaging methods are not necessarily used perfectly simultaneously but are initiated with a time interval. The control unit can for example bring about dispensing of an X-ray contrast medium and put back dispensing of an ultrasound contrast medium until it detects the "switched on" operating state for the ultrasound device and then adds the ultrasound contrast medium to the mixed solution at short notice.

If this embodiment is selected, in which mixing of the mixed solution takes places at the same time as operation of the image recording devices, it may be provided that the mixing unit for the mixed solution provides a volume which is smaller than the full volumes of the containers, so the mixed solution is only produced immediately before injection of the respective quantity into the body of the patient. In other words, the mixed solution does not necessarily have to be produced in a large container, into which two partial solutions fit, at the start, rather it can, on demand, be produced in a smaller volume.

Instead of a relatively simple valve, the device for controlling dispensing of fluid may also comprise a pump for pumping the fluid from the respective container into the mixing unit. The pump thus creates the required pressure differential to bring the fluid from the respective container into the mixing unit. In this case it is in particular not necessary for the container to be connected at a point which is higher than the mixing unit, whereby the exit pressure for the fluid would be provided by the force of gravity.

To facilitate the mixing process an agitator can be provided in the mixing unit. This may be a simple beater or two contra-rotating gearwheels for example.

According to a preferred embodiment a device for controlling the temperature of the mixed solution can be arranged in the mixing unit or on a conveying path from the mixing unit to the syringe. The mixed solution can thus be brought from refrigeration or room temperature to the patient's body temperature, so the patient does not regard injection of the mixed solution as unpleasant. This measure would be expedient with all injections. In the present case no significant complication of the injector according to the invention is involved.

In a preferred embodiment a further pump is provided, for example a pump with piezo actuators, with the aid of which the mixed solution is pumped from the mixing unit into the syringe. Owing to the pump it is not necessary in this case either to arrange the mixing unit so it is higher than the patient in order to thus profit from the force of gravity. The pump provides the requisite pressure.

According to the method of the invention for facilitating imaging of a patient an injector is provided to which containers containing auxiliary fluids may be connected, a device for controlling dispensing of fluid from connected containers being provided in the mixing unit and this device being electronically controlled by a control unit, it being possible to supply data to the control unit, for example by connection to an image recording device. At least two image recording methods are accordingly determined with which features of patients are to be depicted. Appropriate sample data is supplied to the control unit. Appropriate sample data is either input manually via a user interface (for example by selecting from a menu), or the image recording devices connected to the control unit are switched on and by doing so the control unit is informed of their activation.

The image recording parameters are now selected for the first and second image recording methods and corresponding parameter data is supplied to the control unit. In this case image recording parameters are taken to mean all parameters which may play a part during image recording. In an X-ray system these would for example be the X-ray dose, the enlargement, the number of X-ray images to be recorded in total (at least in terms of size) and the contrast and brightness reproduction on a monitor. The corresponding parameter data is again supplied to the control unit. The selection may also be made in a menu in this case as well. The corresponding parameter data is forwarded directly to the control unit via a user interface or an image recording device connected to the control unit. A calculation is then made for total quantities of auxiliary fluids for the first and second image recording methods in the control unit, activation of the devices for controlling the injector to produce the mixed solution, dispensing of the mixed solution via the injector needle into the patient's body and imaging using the two image recording methods, the two image recording methods either being carried out simultaneously or soon after each other (immediately one after the other or, in particular, alternately).

In a preferred embodiment the operating state data of the image recording devices used for the image recording methods is constantly being acquired, the operating state data is supplied to the control unit and a current requirement for partial solutions from the connected containers in the mixed solution is calculated. This should be taken to mean that at a specific time it is not necessarily desirable for the two total quantities calculated according to the method of the invention to be fully mixed with each other and the thus proportionally composed mixed solution to be supplied. It may be desirable for the proportion of a partial solution to be particularly high in the short term, so only a single partial solution is dispensed. According to the preferred embodiment of the method of the invention the devices for controlling the injector to produce a mixed solution, of which the composition is variable over time, are accordingly activated in a manner that is variable over time.

BRIEF DESCRIPTION OF THE DRAWINGS

A particular embodiment of the invention will now be described with reference to the drawing, in which:

The FIGURE shows diagrammatically the components of an injector according to the present invention.

DETAILED DESCRIPTION OF INVENTION

The injector according to the invention shown in the FIGURE comprises for injection an injection tube 10 that ends in a syringe 12 which is introduced into the patient's veins in order to introduce fluid into the patient's body via the tube 10. In the present case an injection solution is not supplied from a single container, rather the solution to be injected is initially produced as a mixed solution in a mixing unit 14. The mixed solution hereby comprises auxiliary fluids for image recording methods. Two different image recording methods are carried out simultaneously or soon after one another, for which reason at least two auxiliary fluids have to be introduced into the patient simultaneously. There is a plurality of auxiliary fluids of this kind available to the mixing unit 14 in corresponding containers 16, 18, 20 22, 24 and 26.

By way of example there is an X-ray contrast medium in a container 16 connected to the mixing unit for the event that X-rays are to be taken, and in a container 20 there is an ultrasound contrast medium. There is a pharmaceutical auxiliary in a container 18, such as saline, hydrochloric acid, trometamol, sodium calcium edetate, water, etc., which can in each case be added to a mixed solution to "dilute" it.

A container 22 for a medicine is also provided, the medicine being for example one which is intended to compensate adverse effects from one of the contrast mediums in containers 16 or 20. There is also a genetic tracer for example in a container 24 which is used in the case of positron emission tomography (PET). Containers for nanoparticle contrast mediums and molecular and genetic markers may also be provided. Finally there is a container 26 for radiopharmaceuticals which, as is conventional, comprises a casing sealed against radiation (shown here by bolder lines).

The containers 16, 18, 20, 22, 24, 26 are conventionally bottles which have a more or less standard shape, so they may be held in a corresponding holding device. It is essential that they are connected to the mixing device 14 in some way. Hollow needles, which simply pierce a rubber stopper in the bottles, although the design thereof may also be different, may be used for this purpose. A connection and pump unit 28 is provided for each container 16 to 26. These are pumps that can be electronically controlled by a control unit 30 and prevent fluid from issuing freely from the containers 16 to 26 into the mixing unit 14 and on the other hand individual fluid doses can be brought into the mixing unit 14 in a purposefully electronically controlled manner. The control unit 30 has a display and operating unit 32 via which data can be input.

It is possible to input which image recording methods should be used with which parameters only via the display and operating unit 32. The control unit then establishes which fluids have to be mixed in the mixing unit 14 to give the mixed solution and in what sub-quantities they have to be prepared. The control unit 30 then activates the connection and pump units 28 of individual containers 16 to 26 accordingly.

In the illustrated embodiment the control unit 30 is connected by an interface 34 to the individual modalities, i.e. the individual image recording devices. A first modality is for example an X-ray unit, an nth modality is for example an ultrasound device. The control unit can therefore be informed via operation of the modalities themselves about which modalities are being used. If for example the X-ray unit and the ultrasound device are switched on and ready for image recording, this is communicated to the control unit 30 via the interface 34. The control unit 30 can activate the connection and pump units 28 accordingly to produce a suitable mixed solution in the mixing unit 14. In the present case of switching on only the X-ray unit and the ultrasound device, the control unit will establish that, for example, 6 ml of the pharmaceutical auxiliary from container 18 are required as the base solution, 30 ml of the X-ray contrast medium are required from container 16, and 14 ml of the ultrasound contrast medium are required from container 20. The control unit 30 activates the connection and pump units 28 pertaining to the respective containers 16, 18 and 20 accordingly. These may be simultaneously activated or one immediately after the other.

The mixing unit 14 is shown smaller here than the containers 16 to 26. However this is basically only due to the diagrammatic illustration. The mixing unit 14 can have a mixing volume which is greater than the filling volume of the individual containers 16 to 26. However, this does not necessarily have to be the case; the mixing volume can also be much smaller. In the latter case the mixed solution would not be fully produced at the start, rather in portions, i.e. in partial volumes, immediately before injection into the patient.

An agitator can be provided in the mixing unit 14 (not shown in FIG. 1) to suitably mix the partial solutions from the containers 16 to 26 to give a mixed solution. Downstream of the mixing unit 14 is shown a temperature-control device 36 which brings the mixed solution to the patient's body temperature and thus makes injection of the fluid more pleasant for the patient. Arranged downstream of the temperature-control device 36 is a pump unit 38 which produces the required pressure to pump the mixed solution from the mixing unit 14, which passes though the temperature-control device 36, into the tube 10 and hence through the syringe 12. As a result of using pumps 28 and 38, in contrast to when conventional infusions are used, it is in principle no longer necessary to work with pressure generated by gravity, i.e. to arrange individual fluid containers higher than the patient ultimately.

The invention makes it possible to provide a large number of modalities in one system and to in each case purposefully produce for use of a plurality of these modalities an infusion solution as a mixed solution which contains the correct quantity of auxiliary fluids for the respectively used image recording method. A single infusion needle 12 is sufficient and the patient is not excessively stressed by the application of a plurality of infusions.

The invention claimed is:

1. A system for injecting a solution into the body of a patient during a medical examination, comprising:
    a plurality of auxiliary media that are respectively used for a plurality of different image recording modalities combined in the medical examination, the plurality of different image recording modalities comprising angiographic X-ray, computer tomography, positron emission tomography, single position emission computer tomography, ultrasound, magnetic resonance imaging, fluorescence imaging, optical coherence tomography and combinations thereof;
    a mixing unit that mixes the plurality of auxiliary media in order to form the solution for the plurality of different image recording modalities; and
    an injector that conveys the mixed solution to the patient via an access opening in the body,
    wherein the system comprises a plurality of different image recording devices used for the plurality of different image recording modalities.

2. The systems as claimed in claim 1, wherein the auxiliary media comprises a fluid or a powder.

3. The system as claimed in claim 1, wherein a plurality of containers hold the auxiliary media and are connected to the mixing unit such that the containers dispense the auxiliary media into the mixing unit.

4. The system as claimed in claim 1, wherein the different imaging recording modalities are selected from the group consisting of: angiographic X-ray, computer tomography, PET, SPECT, extracorporeal MRI, intravascular MRI, extracorporeal ultrasound, intravascular ultrasound, fluorescence imaging, optical coherence tomography and combinations thereof.

5. The system as claimed in claim 1, wherein the auxiliary media are selected from the group consisting of: contrast medium, marker, tracer, medicine, and combinations thereof.

6. The system as claimed in claim 3, wherein the containers comprises bottles with a pierceable stopper.

7. The system as claimed in claim 6, wherein the mixing unit comprises a holder that holds the bottles and a plurality of hollow needles for piercing the stoppers.

8. The system as claimed in claim 3, further comprising a plurality of devices that each separately control the dispensing of the auxiliary media from one container into the mixing unit.

9. The system as claimed in claim 8, wherein the devices are electronically controlled independent of each other by a control unit.

10. The system as claimed in claim 9, wherein:
    the control unit is connected to the image recording devices used for the image recording modalities,
    the control unit obtains parameter data relating to image recordings from the image recording devices, and
    the control unit determines activation signals for the devices from the parameter data for controlling the dispensing of the auxiliary media.

11. The system as claimed in claim 10, wherein:
    the control unit receives operating state data for the image recording devices, and the activation signals are emitted as a function of the operating state data.

12. The system as claimed in claim 6, wherein the mixing unit volume is smaller than the collective container volumes, such that the solution is only produced immediately before injection of the solution into the body of the patient.

13. The system as claimed in claim 8, wherein each device comprises a pump for pumping the fluid from one container into the mixing unit.

14. The system as claimed in claim 1, wherein the mixing unit comprises an agitator to assist the mixing process.

15. The system as claimed in claim 1, wherein a temperature controller for controlling the temperature of the solution is arranged in the mixing unit or on a conveying path from the mixing unit to the access opening in the body.

16. The system as claimed in claim 1, wherein:
the injector is a syringe, and
a pump pumps the mixed solution from the mixing unit into the syringe.

17. A method for facilitating medical imaging of a medical patient, comprising:
selecting a plurality of auxiliary media used for a plurality of different image recording modalities, the plurality of different image recording modalities comprising angiographic X-ray, computer tomography, positron emission tomography, single position emission computer tomography, ultrasound, magnetic resonance imaging, fluorescence imaging, optical coherence tomography and combinations thereof;
providing a mixing device that is controlled by a control unit for mixing the auxiliary media;
establishing first and second image recording modalities that depicts desired features of the patient;
supplying sample data that corresponds to the patient features to the control unit;
selecting image recording parameters for the first and second image recording modalities;
supplying parameter data that corresponds to the image recording parameters to the control unit;
calculating desired quantities of auxiliary media for the first and second image recording modalities in the control unit;
activating the mixing device to mix the auxiliary media and thereby produce a solution;
dispensing the solution via an access opening in the body of the injector into the body of the patient; and
imaging using the at least two image recording modalities.

18. The method as claimed in claim 17, further comprising:
repeating an acquisition of the operating state data of the image recording devices used for the image recording modalities;
supplying the operating state data to the control unit;
calculating a current requirement for the solution, and
producing a variable amount of solution based on the current requirement.

19. The system as claimed in claim 10, wherein the imaging recording devices are operated:
simultaneously by injecting the solution into the body of the patient at one time, or
alternatively by injecting the solution into the body of the patient containing an auxiliary media used for an alternative imaging recording device depending on the activation signals.

* * * * *